(12) United States Patent
Plos et al.

(10) Patent No.: US 7,182,791 B2
(45) Date of Patent: Feb. 27, 2007

(54) COMPOSITION AND METHOD OF DYEING KERATIN FIBERS COMPRISING AT LEAST ONE HETEROALKYL GROUP COMPRISING AT LEAST ONE NINHYDRIN DERIVATIVE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 396 days.

(21) Appl. No.: 10/898,371

(22) Filed: Jul. 26, 2004

(65) Prior Publication Data
US 2005/0060818 A1    Mar. 24, 2005

Related U.S. Application Data

(60) Provisional application No. 60/499,376, filed on Sep. 3, 2003.

(30) Foreign Application Priority Data

Jul. 25, 2003   (FR) ................... 03 09177
Mar. 4, 2004    (FR) ................... 04 02244

(51) Int. Cl.
*A61K 7/13*    (2006.01)
(52) U.S. Cl. ............ 8/405; 8/406; 8/407; 8/410; 8/411; 8/421; 8/437; 8/607; 568/327
(58) Field of Classification Search ............... 8/405, 8/406, 407, 410, 411, 421, 437, 607; 568/327
See application file for complete search history.

(56) References Cited

FOREIGN PATENT DOCUMENTS

| DE | 43 17 855 A | 12/1994 |
|---|---|---|
| DE | 4317855 A1 * | 12/1994 |
| DE | 197 17 222 | 10/1998 |
| DE | 197 45 355 | 4/1999 |
| DE | 198 45 481 | 4/2000 |

OTHER PUBLICATIONS

English Abstract of the Patent No. DE 4317855 A1.*
STIC Search Report (Aug. 7, 2006).*
Heffner R. J., et al. Synthetic routes to ninhydrins preparation of ninhydrin, 5-methoxyninhydrin, and 5-(methylthio)ninhydrin, Synth. Commun., 21, 2231-2256 (1991).
Almog J., et al., 5-methylthio ninhydrin and related compounds: a novel class of fluorogenic fingerprint reagents, Forens, Sci., 37, 688-694 (1992).
Della E. W., et al., Synthesis of fingerprint reagents: aromatic nucleophilic substitution as a route to 5 substituted ninhydrins, synthesis, 12, 2119-2123 (1999).
English Language Abstract of DE 197 17 222.
English Language Abstract of DE 197 45 355.
English Language Abstract of DE 198 45 481.
French Search Report for FR 03/09177 (The French Priority Application for U.S. Appl. No. 10/98,371, the present application) Dated Jun. 23, 2004, Examiner Werner.
Database WPI, Derwent Publications Ltd., London, GB; AN 1973-22659U, XP002285499.
English language Derwent Abstract of DE 43 17 855 A, Dec. 1, 1994.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

A composition and method for dyeing keratin materials, comprising, in a medium that is suitable for dyeing, at least one compound of formula (I)

$$R-X-\underset{\text{(indane-1,2,3-trione)}}{\text{(I)}}$$

wherein
X is chosen from sulphur atoms and selenium atoms,
R is chosen from hydrogen, $C_1$–$C_9$ alkyl groups, cyano groups, halo groups, $C_1$–$C_6$ alkoxy groups, amino groups, ($C_1$–$C_6$ alkyl)amino groups, hydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups. Dyeing kits are also disclosed.

25 Claims, No Drawings

COMPOSITION AND METHOD OF DYEING KERATIN FIBERS COMPRISING AT LEAST ONE HETEROALKYL GROUP COMPRISING AT LEAST ONE NINHYDRIN DERIVATIVE

This application claims benefit of U.S. Provisional Application No. 60/499,376, filed Sep. 3, 2003 and French Application No. 0309177 filed Jul. 25, 2003.

Disclosed herein is a composition for dyeing keratin materials, such as hair, comprising at least one heteroalkyl group comprising at least one ninhydrin derivative, for example, combined with a compound comprising at least one primary or secondary amine functional group or combined with a compound comprising at least one activated methylene functional group. Also disclosed herein is a method for dyeing keratin materials, such as hair and a multi-component dyeing agent used for carrying out such a method.

For a long time, many people have sought to modify the color of their skin, of their eyelashes or of their hair, such as to mask their gray hair. To do this, several technologies have been developed.

It is a known practice to dye human keratin fibers, such as hair, with dyeing compositions comprising oxidation dye precursors, generally called oxidation bases. These oxidation bases are colorless or slightly colored compounds which, when combined with oxidizing products, can give rise, through a process of oxidative condensation, to colored compounds. These dyes are insoluble and are trapped inside the hair fiber.

It is also generally known that it is possible to vary the shades obtained with these oxidation bases by combining them with couplers or color modifiers. The variety of molecules used at the level of the oxidation bases and the couplers allows a rich palette of colors to be obtained.

The colors obtained can exhibit good fastness to shampoo. However, the oxidation reaction occurs with the aid of oxidizing products, such as hydrogen peroxide in a basic medium. These oxidizing agents attack the keratin of the hair, wherein the cosmetic and mechanical properties of the keratin can deteriorate considerably in the event of repeated dyeing.

It is also a known practice to dye human keratin fibers by direct dyeing, comprising in applying to the keratin fibers direct dyes which are colored and dyeing molecules having affinity for the fibers. There may be mentioned, by way of examples, of direct dyes which are conventionally used, nitro dyes, benzene dyes, anthraquinone dyes, nitropyridine dyes, azo dyes, cationic azo dyes, xanthene dyes, acridine dyes, azine dyes or dyes of the triarylmethane type or natural dyes.

The colors obtained, through direct dyeing, can be very chromatic and do not bring about chemical degradation of keratin, but may have the disadvantage of being only temporary or semi-permanent, that is to say of fading, at best, after only 4 to 5 shampoos.

A need therefore remains for systems and methods for dyeing which allow good fastness to be obtained without involving the use of oxidizing agents which are likely to damage keratin materials.

The inventor has discovered that the use of at least one heteroalkyl group comprising at least one ninhydrin derivatives, which is described in greater detail below, makes it possible to dye keratin materials, such as hair, with fastness equivalent or even superior to that obtained by oxidation dyeing, in the absence of strong oxidizing agents, which thereby can better preserve the keratin materials.

The at least one heteroalkyl group comprising at least one ninhydrin derivatives, mentioned above, are, for example, used in combination with compounds comprising at least one labile hydrogen, such as primary or secondary amines or compounds comprising at least one activated methylene functional group.

In one embodiment, the colors obtained exhibit good chromaticity and are distinguishable, for example, by excellent fastness to washing (through several tens of shampoos).

Disclosed herein, is a method for dyeing keratin materials, comprising including, in a medium that is suitable for dyeing, at least one composition comprising at least one compound of formula (I) or its tautomeric form:

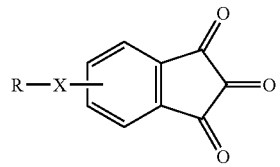

wherein

X is chosen from sulphur atoms and selenium atoms,

R is chosen from hydrogen, linear and branched $C_1$–$C_9$ alkyl groups, cyano groups, halo groups, such as chloro, iodo, bromo and fluoro groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_{1-6}$ alkyl) groups, ($C_{1-6}$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, such as ammonio, imidazolio and pyridinio groups, and aromatic groups comprising at least 5 members, wherein the aromatic group is chosen from monocyclic and polycyclic aromatic groups, comprising fused and non-fused rings, optionally comprising at least one heteroatom chosen from nitrogen, oxygen, sulphur and phosphorus.

The monocyclic or polycyclic aromatic group R can be chosen, for example, from pyrrolyl, thiophenyl, furanyl, pyrazolyl, imidazolyl, phenyl, pyranyl, pyridinyl, pyrimidinyl, indolyl, quinolinyl, carbazolyl, chromenyl, biphenyl and naphthalenyl groups.

The monocyclic or polycyclic aromatic group R can be chosen from thiophenyl, phenyl and naphthalenyl groups.

For example, the monocyclic or polycyclic aromatic group R may be substituted with at least one group chosen from halo groups, such as chloro, iodo, bromo and fluoro groups, $C_1$–$C_6$ alkyl groups, hydroxyl groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio ($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, such as ammonio, imidazolio and pyridinio groups.

Such compositions are, for example, useful for dyeing keratin fibers, such as hair.

The compounds of formula (I) also include the corresponding addition salts of acids and addition salts of bases.

The above ninhydrin derivatives of formula (I), as disclosed herein, may be used in a cosmetically acceptable medium generally comprising a large fraction of water. Generally, when they are dissolved in such an aqueous medium, the ninhydrin derivatives of formula (I) are in hydration equilibrium with the geminal diol form (or carbonyl hydrate) corresponding to the following formula (I)a:

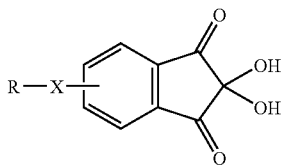
(I)a

When reference is made, as disclosed herein, to ninhydrin derivatives of formula (I), they consequently always include not only the compounds of formula (I) but also the corresponding hydrated forms of formula (I)a.

Non-limiting examples of ninhydrin derivatives which can be used, as disclosed herein, for dyeing hair fibers include:

(a) 5-(methylthio)ninhydrin
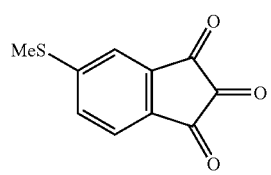

(b) 5-(isopropylthio)ninhydrin
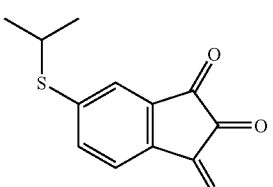

(c) 5-(thiocyano)ninhydrin
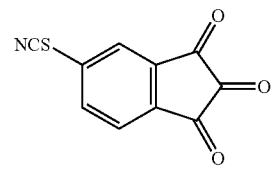

(d) 5-(butylthio)ninhydrin
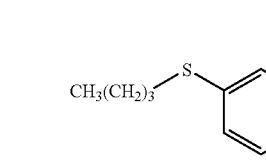

(e) 5-(octylthio)ninhydrin
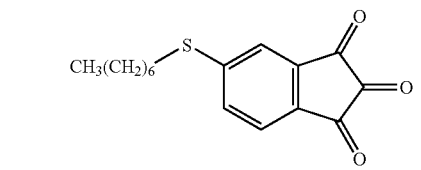

(f) 5-(phenylsulphanyl)ninhydrin
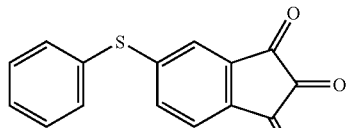

(g) 5-(methylselenio)ninhydrin
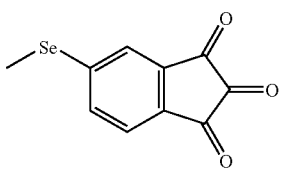

(h) 5-(pentylselenio)ninhydrin
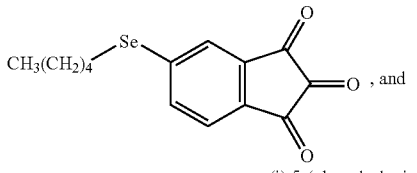, and (i) 5-(phenylselenio)ninhydrin
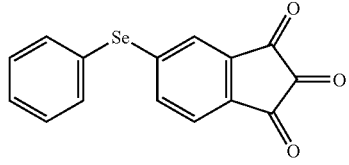

The ninhydrin derivatives, as disclosed herein, are known in the art. The synthesis of the above ninhydrin derivatives (a) to (i) is described in the following publications:

(a) 5-(methylthio)ninhydrin: Heffner R. J., Joullié M. M., Synthetic routes to ninhydrins preparation of ninhydrin, 5-methoxyninhydrin, and 5-(methylthio)ninhydrin, Synth. Commun. 1991, 21, 2231–2256.

(b) 5-(isopropylthio)ninhydrin: Almog J., Hirschfeld A., Frank A., Grant H., Harel Z., Ittah Y., 5-methylthio ninhydrin and related compounds: a novel class of fluorogenic fingerprint reagents, Forens. Sci. 1992, 37, 688–694.

(c) 5-(thiocyano)ninhydrin: Almog J., Hirschfeld A., Frank A., Grant H., Harel Z., Ittah Y., 5-methylthio ninhydrin and related compounds: a novel class of fluorogenic fingerprint reagents, Forens. Sci. 1992, 37, 688–694.

(d) 5-(butylthio)ninhydrin: Della E. W., Janowski W. K., Pigou P. P., Taylor B. M., Synthesis of fingerprint reagents: aromatic nucleophilic substitution as a route to 5 substituted ninhydrins, synthesis, 1999, 12, 2119–2123.

(e) 5-(heptylthio)ninhydrin: Della E. W., Janowski W. K., Pigou P. P., Taylor B. M., Synthesis of fingerprint reagents: aromatic nucleophilic substitution as a route to 5 substituted ninhydrins, synthesis, 1999, 12, 2119–2123.

(f) 5-(phenylsulphanyl)ninhydrin: Della E. W., Janowski W. K., Pigou P. P., Taylor B. M., Synthesis of fingerprint reagents: aromatic nucleophilic substitution as a route to 5-substituted ninhydrins, synthesis, 1999, 12, 2119–2123.

(g) 5-(methylselenio)ninhydrin: Della E. W., Janowski W. K., Pigou P. P., Taylor B. M., Synthesis of fingerprint reagents: aromatic nucleophilic substitution as a route to 5-substituted ninhydrins, synthesis, 1999, 12, 2119–2123.

(h) 5-(pentylselenio)ninhydrin: Della E. W., Janowski W. K., Pigou P. Synthesis of fingerprint reagents: aromatic nucleophilic substitution substituted ninhydrins, synthesis, 1999, 12, 2119–2123.

(i) 5-(phenylselenio)ninhydrin: Della E. W., Janowski W. K., Pigou P. Synthesis of fingerprint reagents: aromatic nucleophilic substitution substituted ninhydrins, synthesis, 1999, 12, 2119–2123.

As disclosed herein, the ninhydrin derivatives of formula (I) may be used alone for dyeing keratin materials. For example, these compounds are capable of generating colored molecules with the amine functional groups of keratin (colored reaction).

It may also be possible to use the compounds of formula (I) together with at least one activator which makes it possible to modify the kinetics of reaction of the ninhydrin compound with the keratinous material. Such an activator may be chosen from oxidizing agents; reducing agents; Brönsted acids; metal catalysts, such as catalysts based on a transition metal, such as iron, platinum and palladium; proteins, such as enzymes; compounds which modify the ionic strength of the medium, such as NaCl salts; compounds comprising at least one labile hydrogen chosen from those comprising at least one primary or secondary amine functional group and those comprising at least one activated methylene functional group. It is also possible to use a mixture of such compounds.

The compounds with at least one primary amine or a secondary amine functional group include, for example, aromatic amines.

Non-limiting examples of such aromatic amines include: N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, dibromohydrate of 2,5-dihydroxy-4-morpholinoaniline, 2-, 3- and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino-4-hydroxybenzoic acid, 4-amino-3-hydroxybenzoic acid, 2-amino-, 3-amino and 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, corresponding to formula (II)

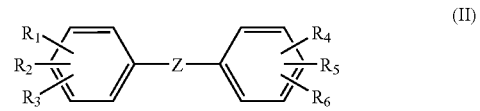

wherein $R^1$ is chosen from hydroxyl and amino groups optionally substituted with at least one $C_{1-4}$ alkyl, $C_{1-4}$ hydroxyalkyl and $(C_{1-4}$ alkoxy)-$(C_{1-4}$ alkyl) group, $R^2$, $R^3$, $R^4$, $R^5$ and $R^6$, which may be identical or different, are chosen from hydrogen, hydroxyl groups and amino groups, optionally substituted with at least one $C_{1-4}$ alkyl, $C_{1-4}$ hydroxyalkyl and $(C_{1-4}$ alkoxy)-$(C_{1-4}$ alkyl) group, and carboxylic and sulphonic acid groups, Z is chosen from a direct bond, saturated and unsaturated $C_{1-4}$ hydrocarbon chains, optionally hydroxylated, carbonyl, sulphonyl and imino groups, oxygen and sulphur atoms, and groups of formula Q—$(CH_2$—P—$CH_2$_Q')$_o$, wherein P is chosen from a direct bond, —$CH_2$— groups and —CHOH— groups, o is a number ranging from 1 to 4, Q and Q', which may be identical or different, are chosen from oxygen atoms, $NR^7$ groups, wherein $R^7$ is chosen from hydrogen, $C_{1-4}$ alkyl and $C_{1-4}$ hydroxyalkyl groups, and O—$(CH_2)_p$NH and NH—$(CH_2)_{p'}$—O groups wherein p and p' are 2 and 3.

The nonaromatic primary and secondary amines are chosen, for example, from 2-aminoethanol, 2-methoxyethylamine, 2-ethoxyethylamine, 2-(2-aminoethoxy)ethanol, 2- and 3-aminopropanol, 2,3-dihydroxypropylamine, 4-hydroxypropyl-amine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines such as glucamine, D-glucosamine, D-galactosamine, 1,2-diaminoethane, 1,2- and 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

The compounds comprising at least one activated methylene functional group are chosen, for example, from: 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid,1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone, and 1-methyl-3-phenyl-2-pyrazolinone.

These primary and secondary amines and these compounds comprising activated methylene functional groups and other compounds comprising at least one labile hydrogen are also described in Patent Application Nos. DE 43 17 855, DE 197 17 222, DE 198 45 481 and DE 197 45 355 wherein the compounds are used for dyeing keratin fibers in combination with compounds different from the ninhydrin derivatives of formula (I).

Generally, when the ninhydrin derivatives of formula (I) are used in combination with a primary or secondary amine or with a compound comprising at least one activated methylene functional group, it is necessary to store these different reagents separately in order to avoid a premature color reaction. The reagents are then only brought into contact immediately before application to the hair by freshly mixing two compositions, respectively comprising, the ninhydrin derivatives and the compounds comprising at least one labile hydrogen. The reagents may also be brought into contact directly with the hair by successive application of the various reagents.

Further disclosed herein is a multi-component dyeing agent comprising
  at least one first component, a composition (a), comprising at least one ninhydrin derivative of formula (I), and
  at least one second component, a composition (b), comprising at least one compound comprising at least one primary or secondary amine functional group or at least one compound comprising at least one activated methylene functional group, as described above.

This multi-component dyeing agent can, for example, be in the form of a multi-compartment kit, comprising at least one first compartment comprising at least one compound comprising at least one ninhydrin derivative of formula (I) and at least one second compartment comprising at least one compound comprising at least one compound comprising at least one primary or secondary amine functional group or at least one compound comprising at least one activated methylene functional group.

Also disclosed herein is a dyeing cosmetic composition comprising at least one ninhydrin derivative of formula (I) and at least one cosmetic active ingredient.

The cosmetic active ingredients present in the cosmetic compositions, as disclosed herein, may be chosen, for example, from vitamins, saccharides, oligosaccharides, hydrolyzed and non-hydrolyzed, and modified and non-modified polysaccharides, amino acids, oligopeptides, peptides, hydrolyzed and non-hydrolyzed, and modified and non-modified proteins, polyamino acids, enzymes, fatty acids and branched and non-branched alcohols, animal, vegetable and mineral waxes, ceramides and pseudoceramides, hydroxylated organic acids, UV-screening agents, antioxidants and anti-free-radical agents, chelating agents, anti-dandruff agents, seborrhoea-regulating agents, smoothing agents, cationic, anionic, nonionic and amphoteric surfactants, cationic, anionic, neutral and amphoteric polymers, organomodified and non-organomodified silicones, mineral, vegetable and animal oils, polyisobutenes and poly(α-olefins), fatty esters, anionic polymers in dissolved and dispersed form, nonionic polymers in dissolved and dispersed form, reducing agents, solvents, hair dyes, such as direct dyes and oxidation dye precursors (bases and couplers) different from the claimed compounds comprising at least one primary or secondary amine functional group, oxidants, such as hydrogen peroxide optionally combined with per-salts, pigments, and mixtures thereof.

The cosmetic active ingredient can, for example, be present in an amount ranging from 0.001 to 50% by weight, for example, from 0.01 to 20% by weight, and further, for example, from 0.1 to 10% by weight, relative to the total weight of the cosmetic composition.

For example, in one embodiment of the disclosed dyeing cosmetic composition, the cosmetic active ingredient is chosen from surfactant and polymeric (polymer) agents, wherein these agents can be of a nonionic, cationic, anionic or amphoteric nature.

In one embodiment, the hair dyeing compositions, as used herein, are stable during storage when they contain, as sole dyeing reagents, ninhydrin derivatives of formula (I) or (Ia). In a further embodiment, when they contain both ninhydrin derivatives of formula (I) or (Ia) and compounds comprising at least one labile hydrogen, such as primary or secondary amines or compounds comprising at least one activated methylene functional group, these compositions must be used immediately after mixing the composition comprising the ninhydrin derivatives of formula (I) or (Ia) with that comprising the at least one labile hydrogen comprising compound(s).

These ready-to-use dyeing compositions, whether they are stable during storage or prepared immediately before use, have, for example, a pH ranging from 2 to 12, and further, for example, from 3 to 11.

The amount of ninhydrin derivatives of formula (I), present in the ready-to-use dyeing compositions, ranges, for example from 0.0001% and 30% by weight, relative to the total weight of the composition.

The compounds comprising at least one labile hydrogen, which are used in combination with the ninhydrin derivatives of formula (I), are present, for example, in an amount ranging from 0.0001% to 30% by weight, relative to the total weight of the composition.

Further disclosed herein is a hair dyeing method comprising applying, to the hair, a ready-to-use hair dyeing composition as described above. This composition is left in contact with the hair fibers for a time sufficient to obtain the desired color. This leave-in time generally ranges from 5 minutes to 1 hour, and, for example, from 15 to 30 minutes. The colored reaction between the ninhydrin derivatives and the amine functional groups of the keratin or the compounds, which may be present, comprising at least one labile hydrogen, may be accelerated by heating the hair impregnated with the dyeing composition. The heating temperature, for example, should not exceed 80° C., and is less than or equal to 60° C.

After obtaining the desired color, the hair is rinsed and washed.

When compounds comprising at least one labile hydrogen, such as primary or secondary amines or compounds comprising at least one activated methylene functional group are used, the application of the reagents taking part in the colored reaction may also be performed in two stages. For example, it is possible to successively apply two different compositions respectively comprising at least one ninhydrin derivative of formula (I) and at least one compound comprising at least one primary or secondary amine functional group or at least one activated methylene functional group.

Also disclosed herein is a two-stage dyeing method comprising applying, to the hair, one after the other, in any order, a composition (a), comprising at least one ninhydrin derivative of formula (I) and a composition (b), comprising at least one compound comprising at least one primary or secondary amine functional group or at least one compound comprising at least one activated methylene functional group.

The separate application of the two reactive compositions has the advantage of avoiding the handling of colored compositions and thus reduces the risks of staining materials such as clothes.

The applicant observed that satisfactory hair colors were also obtained when an intermediate rinsing stage was inserted between the application of the first composition and the application of the second composition.

In a similar manner to that described above, hair impregnated with composition (a) and/or (b) may be heated, for example, to a temperature of 80° C., and further, for example, to a temperature not exceeding 60° C., such heating making it possible to accelerate the colored reaction and to shorten the leave-in time.

EXAMPLES

The following composition was prepared:

| | |
|---|---|
| 5-(phenylsulphanyl)ninhydrin (=hydrate of the compound of formula (f)) | $10^{-2}$ moles |
| Ethanol | 50 g |
| NaOH | qs pH 7 |
| Distilled water | qs 100 g |

This composition was applied to two locks of natural and permanently waved hair which was 90% white, of 1 g each. The bath ratio was 5, the leave-in time 30 minutes and the temperature 60° C. At the end of the leave-in time, the locks were rinsed and then washed with a standard shampoo.

The color intensity was evaluated by colorimetry according to the CIELAB system using a Minolta CM3600d calorimeter (illuminant D65, angle of observation: 10°, specular component included).

The CIELAB scoring system defines a colorimetric space wherein each color is defined by three parameters ($L^*$, $a^*$ and $b^*$):

- the parameter $L^*$ reflects the clarity of the color, the value of $L^*$ being equal to 0 for black and equal to 1 for absolute white. The higher the value of $L^*$, the less intense the color,
- the parameter $a^*$ corresponds to the axis of the green-red antagonist pair and the parameter $b^*$ to the axis of the blue-yellow antagonist pair.

The table below shows the parameters $L^*$, $a^*$ and $b^*$ of the locks of natural hair and of permanently waved hair before and after the increase in the color, as $\Delta E$ defined by the equation below:

$$\Delta E = \sqrt{(L^*_{final} - L^*_{initial})^2 + (a^*_{final} - a^*_{initial})^2 + (b^*_{final} - b^*_{initial})^2}$$

$\Delta E$ reflects the overall variation in color. The higher the variation in color, the higher its value.

| Hair | | $L^*$ | $a^*$ | $b^*$ | $\Delta E$ | Color |
|---|---|---|---|---|---|---|
| Natural | Before dyeing | 62.80 | −0.10 | 9.52 | — | — |
| Natural | After dyeing | 25.86 | −4.75 | −7.93 | 45.72 | blue |
| Permanently waved | Before dyeing | 62.58 | −0.28 | 13.46 | — | — |
| Permanently waved | After dyeing | 21.91 | 1.20 | −2.64 | 46.23 | black |

What is claimed is:

1. A method for dyeing keratin material comprising:
   applying to the keratin material a composition comprising, in a medium that is suitable for dyeing, at least one ninhydrin compound of formula (I)

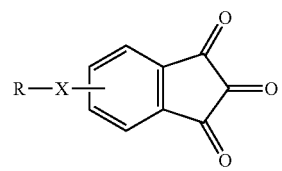

wherein
   X is chosen from sulphur atoms and selenium atoms, and
   R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl) amino groups, mono- and dihydroxy($C_1$–$C_6$ alkyl) amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused or non-fused rings, optionally comprising at least one heteroatom chosen from nitrogen, oxygen, sulphur and phosphorus.

2. The method according to claim 1, wherein the corresponding protonated groups are chosen from ammonio, imidazolio and pyridinio groups.

3. The method according to claim 1, wherein the monocyclic or polycyclic aromatic group R is chosen from pyrrolyl, thiophenyl, furanyl, pyrazolyl, imidazolyl, phenyl, pyranyl, pyridinyl, pyrimidinyl, indolyl, quinolinyl, carbazolyl, chromenyl, biphenyl and naphthalenyl groups.

4. The method according to claim 3, wherein the monocyclic or polycyclic aromatic group R is chosen from thiophenyl, phenyl and naphthalenyl groups.

5. The method according to claim 3, wherein the monocyclic or polycyclic aromatic group R is substituted with at least one group chosen from halo groups, $C_1$–$C_6$ alkyl groups, hydroxyl groups, $C_1$–$C_6$ alkoxy groups, amino groups, imidazolyl groups, pyridinyl groups, mono- and di($C_1$–$C_6$ alkyl)amino groups, mono- and dihydroxy($C_1$–$C_6$ alkyl)amino groups, tri($C_1$–$C_6$ alkyl)ammonio groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups.

6. The method according to claim 5, wherein the corresponding protonated groups are chosen from ammonio, imidazolio, and pyridinio groups.

7. The method according to claim 1, wherein the composition additionally comprises at least one activator, wherein the activator makes it possible to modify the reaction kinetics of the at least one ninhydrin compound of formula (I) with the keratin material.

8. The method according to claim 7, wherein the at least one activator is chosen from oxidizing agents, reducing agents, Brönsted acids, metal catalysts, proteins, compounds which modify the ionic strength of the medium, and compounds comprising at least one labile hydrogen chosen from compounds comprising at least one primary or secondary amine functional group and compounds comprising at least one activated methylene functional group.

9. The method according to claim 8, wherein the compound comprising at least one primary or secondary amine functional group is chosen from aromatic amines chosen from N,N-dimethyl-p-phenylenediamine, N,N-diethyl-p-phenylenediamine, N-(2-hydroxyethyl)-N-ethyl-p-phenylenediamine, N,N-bis-(2-hydroxyethyl)-p-phenylenediamine, N-(2-methoxyethyl)-p-phenylenediamine, 2,3-, 2,4- and 2,5-dichloro-p-phenylenediamine, 2-chloro-p-phenylenediamine, dibromohydrate of 2,5-dihydroxy-4-morpholinoaniline, 2-, 3- and 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy) ethanol, 4-methylaminoaniline, 3-amino4-(2'-hydroxyethyloxy)aniline, 3,4-methylenediaminoaniline, 3,4-methylenedioxyaniline, 3-amino-2,4-dichlorophenol, 4-methyl-aminophenol, 2-methyl-5-aminophenol, 3-methyl4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, 2-amino-, 3-amino- and 4-aminophenylacetic acid, 2,3-, 2,4-, 2,5-, 3,4- and 3,5-diaminobenzoic acid, 4-amino- and 5-aminosalicylic acid, 3-amino4-hydroxybenzoic acid, 4-amino-3-hydroxybenzoic acid, 2-amino-, 3-amino and 4-aminobenzenesulphonic acid, 3-amino4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino4-hydroxypyrocatechol, aromatic anilines and aromatic phenols comprising another aromatic residue, corresponding to formula (II) below

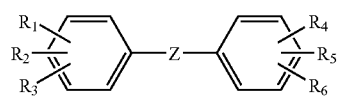

wherein
R$_1$ is chosen from hydroxyl and amino groups optionally substituted with at least one C$_{1-4}$ alkyl, C$_{1-4}$ hydroxyalkyl or (C$_{1-4}$ alkoxy)-(C$_{1-4}$ alkyl) group,
R$_2$, R$_3$, R$_4$, R$_5$ and R$_6$, which may be identical or different, are chosen from hydrogen, hydroxyl groups and amino groups, optionally substituted with at least one C$_{1-4}$ alkyl, C$_{1-4}$ hydroxyalkyl and (C$_{1-4}$ alkoxy)-(C$_{1-4}$ alkyl) groups, and carboxylic and sulphonic acid groups, Z is chosen from a direct bond; saturated and unsaturated C$_{1-4}$ hydrocarbon chains; wherein the hydrocarbon chains are optionally hydroxylated; carbonyl, sulphonyl, and imino groups; oxygen and sulphur atoms; groups of formula Q—(CH$_2$—P—CH$_2$_Q')$_o$ wherein P is chosen from direct bonds and —CH$_2$— and —CHOH— groups, o is a number ranging from 1 to 4, Q and Q', which may be identical or different, are chosen from oxygen atoms, NR$^7$ groups, wherein R$^7$ is chosen from hydrogen, C$_{1-4}$ alkyls and C$_{1-4}$ hydroxyalkyl groups and O—(CH$_2$)$_p$NH or NH—(CH$_2$)$_{p'}$—O groups wherein p and p', which may be identical or different are 2 or 3; and aliphatic amines chosen from 2-aminoethanol, 2-methoxyethylamine, 2-ethoxyethylamine, 2-(2-aminoethoxy)ethanol, 2- and 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2- and 1,3-diaminopropane, 1,3-diamino-2-propanol, 2-(2-aminoethylamino)ethylamine, 2-(2-aminoethylamino)ethanol, 3-(2-aminoethylamino)propylamine and 3-(2-aminoethylamino)propanol.

10. The method according to claim 9, wherein the compound comprising at least one activated methylene functional group is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone, and 1-methyl-3-phenyl-2-pyrazinone.

11. The method according to claim 1, wherein the composition has a pH ranging from 2 to 12.

12. The method according to claim 11, wherein the composition has a pH ranging from 3 to 11.

13. The method according to claim 1, wherein the at least one ninhydrin compound of formula (I) is present in an amount ranging from 0.0001% to 30% by weight, relative to the total weight of the composition.

14. The method according to claim 1, wherein the compound comprising at least one activated methylene functional group or of the compound comprising at least one primary or secondary amine functional group is present in an amount ranging from 0.0001% to 30% by weight, relative to the total weight of the composition.

15. A cosmetic dyeing composition comprising, in a medium that is suitable for dyeing keratin fibers:
at least one ninhydrin compound of formula (I)

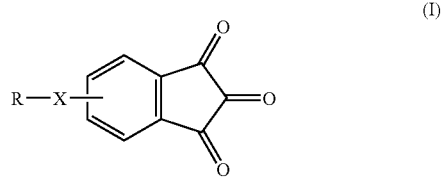

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus; and at least one agent chosen from nonionic, cationic, anionic and amphoteric surfactants and nonionic, cationic, anionic and amphoteric polymers.

16. A ready-to-use cosmetic composition comprising:
at least one ninhydrin compound of formula (I)

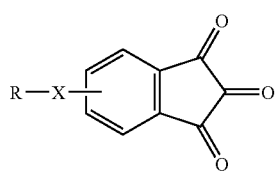

(I)

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus; and at least one compound chosen from compounds comprising at least one primary or secondary amine functional group and compounds comprising at least one activated methylene functional group, and mixtures thereof, wherein the ready-to-use composition is prepared at the time of use.

17. A multi-component dyeing agent for keratin material comprising
at least one first component, comprising at least one ninhydrin compound of formula (I)

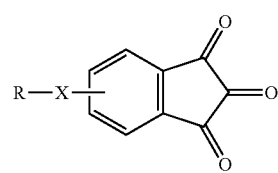

(I)

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus; and at least one second component, comprising at least one activator, wherein said at least one activator makes it possible to modify the reaction kinetics of the at least one ninhydrin compound of formula (I) with the keratin material.

18. A multi-compartment kit for dyeing keratin material comprising: at least one first compartment comprising
at least one ninhydrin compound of formula (I)

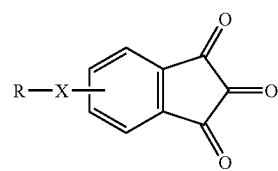

(I)

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl)amino groups, mono- and dihydroxy($C_1$–$C_6$ alkyl)amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus; and at least one second compartment comprising at least one activator, wherein said at least one activator makes it possible to modify the reaction kinetics of the at least one ninhydrin compound of formula (I) with the keratin material.

19. A method for dyeing hair comprising:

applying, to the hair, at least one composition comprising, in a medium that is suitable for dyeing, at least one ninhydrin compound of formula (I)

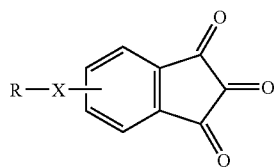

(I)

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl) amino groups, mono- and dihydroxy($C_1$–$C_6$ alkyl) amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus, leaving the composition on the hair for a time sufficient to obtain a desired color, and rinsing and washing the hair.

20. The method according to claim 19, further comprising heating hair impregnated with hair dyeing composition to a temperature up to 80° C.

21. The method according to claim 20, wherein the hair is heated to a temperature of 60° C.

22. A method for dyeing hair comprising applying, to the hair, one after the other, in any order, a first composition comprising at least one ninhydrin compound of formula (I)

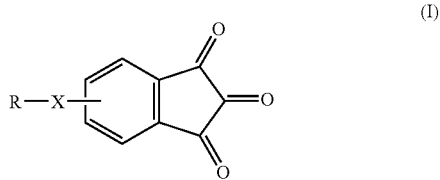

(I)

wherein

X is chosen from sulphur atoms and selenium atoms,

R is chosen from hydrogen, linear and branched $C_1$–$C_9$ alkyl groups, cyano groups, halo groups, $C_1$–$C_6$ alkoxy groups, amino groups, mono- and di($C_1$–$C_6$ alkyl) amino groups, mono- and dihydroxy($C_1$–$C_6$ alkyl) amino groups, tri($C_1$–$C_6$ alkyl)ammonio groups, imidazolyl groups, pyridinyl groups, thio groups, ($C_1$–$C_6$ alkyl)thio groups, thio($C_1$–$C_6$ alkyl) groups, ($C_1$–$C_6$ alkyl)carbonyl groups, hydrogenocarbonyl groups, hydroxycarbonyl groups, ($C_1$–$C_6$ alkoxy)carbonyl groups, nitro groups, sulphonato groups, and corresponding protonated groups, and aromatic groups comprising at least 5 members, wherein the aromatic groups are chosen from monocyclic and polycyclic groups, fused and non-fused rings, optionally comprising at least one heteroatom chosen from nitrogen, oxygen, sulphur and phosphorus; and a second composition comprising at least one activator, wherein said at least one activator makes it possible to modify the reaction kinetics of the at least one ninhydrin compound of formula (I) with the hair.

23. The method according to claim 22, wherein an intermediate rinsing step is inserted between the application of the first composition and the application of the second composition.

24. The method according to claim 22, further comprising heating hair impregnated with the first composition and/or with the second composition to a temperature of 80° C.

25. The method according to claim 24, wherein the hair is heated to a temperature of 60° C.

* * * * *